United States Patent [19]

Jernberg

[11] Patent Number: 4,685,883
[45] Date of Patent: Aug. 11, 1987

[54] LOCAL DELIVERY OF CHEMOTHERAPEUTIC AGENTS FOR THE TREATMENT OF PERIODONTAL DISEASE

[76] Inventor: Gary R. Jernberg, 99 Navaho Ave. Ste. 102, Mankato, Minn. 56001

[21] Appl. No.: 759,513

[22] Filed: Jul. 26, 1985

Related U.S. Application Data

[63] Continuation of Ser. No. 530,999, Sep. 12, 1983, abandoned.

[51] Int. Cl.$^4$ ............................................... A61C 5/00
[52] U.S. Cl. ..................................... 433/215; 433/80; 433/136; 604/890
[58] Field of Search ............... 433/215, 217, 135, 136, 433/80, 229; 604/890, 891, 892, 894, 896, 49, 54, 77; 128/136

[56] References Cited

U.S. PATENT DOCUMENTS

| | | | |
|---|---|---|---|
| 2,174,796 | 10/1939 | Luzzi | 433/136 |
| 2,835,628 | 5/1958 | Saffir | 433/136 |
| 3,811,444 | 5/1974 | Heller et al. | |
| 3,887,699 | 6/1975 | Yelles | |
| 3,972,995 | 8/1976 | Tsuk et al. | |
| 3,991,766 | 11/1976 | Schmitt et al. | |
| 4,001,388 | 1/1977 | Shell | 604/894 |
| 4,121,940 | 10/1978 | Michel et al. | |
| 4,175,326 | 11/1979 | Goodson | 433/80 |
| 4,249,531 | 2/1981 | Heller et al. | |
| 4,250,163 | 2/1981 | Negai et al. | |
| 4,276,880 | 7/1981 | Malmin | 433/80 |
| 4,321,038 | 3/1982 | Porteous | |

OTHER PUBLICATIONS

"Timed-Release Anesthetic Developed", The Washington Post, Mar. 6, 1985.
Goodson, J. M., Haffajee, A. and Socransky, S. S.: Periodontal Therapy by Local Delivery of Tetracycline. J. Clin. Periodontal 6:83, 1979.
Lindhe, J. et al.: Local Tetracycline Delivery Using Hollow Fiber Devices in Periodontal Therapy., J. Clin. Periodontal, 6:141, 1979.
Goodson, J. M. et al.: Monolithic Tetracycline-Containing Fibers for Controlled Delivery to Periodontal Pockets., J. Clin. Periodontal 54:575, Oct. 1983.
The Effect of Long-Term Low-Dose Tetracycline Therapy on the Subgingival Microflora in refractory Adult Periodontitis, K. S. Kornman et al., Journal of Periodontology, 1982:53:604-610.
The Development and in Vitro Evaluation of Acrylic Strips and Dialysis Tubing for Local Drug Delivery, M. Addy et al., Journal of Periodontology, 1982:53:693-699.
Tetracycline and its Derivatives Strongly Bind to and are released from the Tooth Surface in Active Form, P. J. Baker et al., Journal of Periodontology 1983:54:580-585.
Subgingival Metronidazole in Acrylic Resin vs. Chlorhexidine Irrigation in the Control of Chronic Periodontitis, F. I. S. Yeung et al., Journal of Periodontology, 1983:54:651-657.
Subgingival Metronidazole in Dialysis Tubing and Subgingival Chlorhexidine Irrigation in the Control of Chronic Inflammatory Periodontal Disease, W. Z. A. Wan Yusof et al., Journal of R. Clinical Periodontology, 1984:11:166-175.
Comparison of the Immediate Effects on the Subgingival Microflora of Acrylic Strips Containing 40% Chlorhexidine Metronidazole or Tetracycline, M. Addy et al., Journal of Clinical Periodontology, 1984:11:379-386.

(List continued on next page.)

*Primary Examiner*—John J. Wilson
*Attorney, Agent, or Firm*—Merchant, Gould, Smith, Edell, Welter & Schmidt

[57] ABSTRACT

A method for local delivery of chemotherapeutic agent (12) to a localized site in the mouth is disclosed. The method of delivery includes displacement or reflection of gingival tissues (20) from the tooth, in the area to be treated, to facilitate access to the periodontal lesion (16). A biodegradable, time-release microsphere (10) capsulating the chemotherapeutic agent is next positioned in the lesion (16). Accordingly, localized delivery of chemotherapeutic agent (12) continuously over a predetermined period of time is provided.

7 Claims, 12 Drawing Figures

OTHER PUBLICATIONS

Simple Bacteriological Methods to Assess Changes in Subbingival Microflora Produced by Metronidazole-Containing Acrylic Strips Placed into Periodontal Pockets, M. Addy et al., Journal of Clinical Periodontology, 1984:11:467-474.

Slow Release Metronidazole and a Simplified Mechanical Oral Hygiene Regimen in the Control of Chronic Periodontitis, H. N. Newman et al., Journal of Clinical Periodontology, 1984:11:576-582.

Clinical Responses Following Periodontal Treatment by Local Drug Delivery, J. M. Goodson et al., Journal of Periodontology, Supplement 1985:81-87.

Tetracyclines Inhibit Tissue collagenases: Effects of Ingested Low-Dose and Local Delivery Systems, L. M. Golub et al., Journal of Periodontology, Supplement, 1985:93-97.

Freeze-Dried Bone Allografts Combined with Tetracycline in the Treatment of Juvenile Periodontitis, Thomas W. Mabry et al., Journal of Periodontology, 1985:56:74-81.

Periodontal Disease Treatment by Local Drug Delivery, J. M. Goodson, Journal of Periodontology, 1985:56:265-272.

Clinical and Microbiological Effects of Sustained Release chlorhexidine in Periodontal Pockets, A. Stabholz et al., Journal of Clinical Periodontology, 1986:13:783-788.

Gum Disease Alleviated by Pellets, Patricia R. Raber, Dentistry Today, vol. 5, No. 5, Jun. 1986.

Kakehashi, S. and Parakkal, P. F.: Proceedings From the State of the Art Workshop on Surgical Therapy for Periodontitis., J. Periodontal 53:475, 1982.

Genco, R. J.: Antibiotics in the Treatment of Human Periodontal Diseases., J. Periodontal 52:545, 1981.

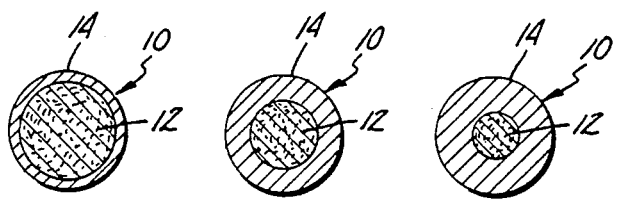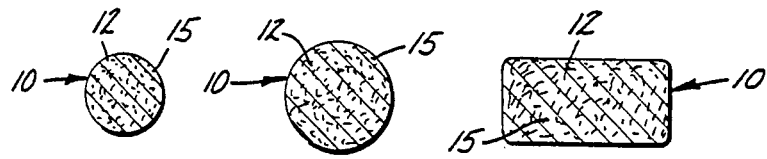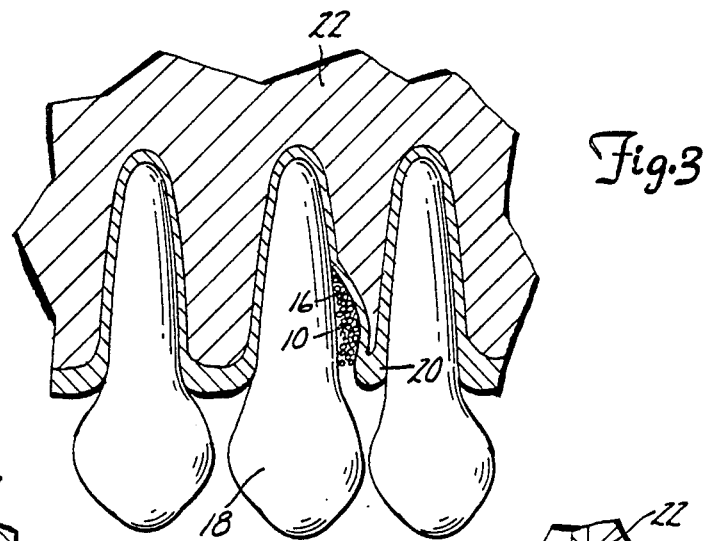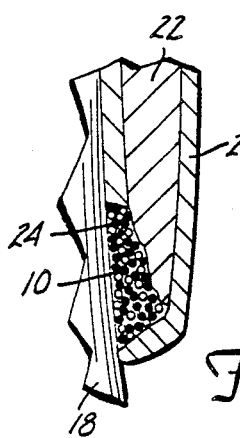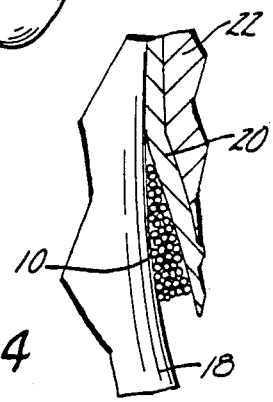

LOCAL DELIVERY OF CHEMOTHERAPEUTIC AGENTS FOR THE TREATMENT OF PERIODONTAL DISEASE

This is a continuation of application Ser. No. 530,999, filed Sept. 12, 1983, now abandoned.

BACKGROUND OF THE INVENTION

Periodontal disease results in progressive loss of gingival (gum) and alveolar (socket) bone support to the tooth and is caused by bacteria which colonize the tooth surface and occupy the gingival crevice area. This often leads to a pathologic deepening of the normal gingival crevice with subsequent formation of a periodontal pocket. Loss of alveolar bone and inflammation of gingival tissues adjacent to the pocket occurs, manifesting in a periodontal lesion.

Periodontal disease is the major cause of tooth loss in adults worldwide. Bacterial plaque is the principal causative agent of periodontal disease.

Routine daily prevention or removal of plaque by the patient is a sine qua non in periodontal therapy. This involves the use of toothbrushes, floss and various other oral hygiene instruments. These devices require motor skill and dexterity. The daily routines for adequate plaque removal require the patient to be diligent, motivated, educated and skillful. Accordingly, such methods are effective only when used by motivated individuals and then often to a limited extent.

Traditional periodontal therapy has also emphasized mechanical removal of soft and hard accretions of bacteria (i.e., plaque and calculus) from the root surface via use of dental instruments placed into the gum crevice to mechanically shear the accretions from the tooth structure. See S. Kakehashi and P.F. Parakkal, *Proceedings from the State of the Art Workshop on Surgical Therapy for Periodontitis*, J. Periodontol 53:475 (1982).

Systemic chemotherapeutic agents have also been used in periodontal therapy. See R.J. Genco, *Antibiotics in the Treatment of Human Periodontal Diseases*, J. Periodontol 52:545 (1981). However, systemic delivery (e.g., oral or intramuscular) often does not provide a strong enough concentration of chemotherapeutic agent over an extended period of time to the specific area where required. In addition, the possibility exists that indigenous bacteria may develop resistance to such a method of therapy.

Recent studies have focused on the use of the local delivery of tetracycline to periodontal lesions via non-degradable hollow fibers placed into the lesion with dental instruments. This method has shown considerable promise in transient elimination or control of localized subgingival bacteria. See J.M. Goodson, A. Haffajee, and S.S. Socransky, *Periodontal Therapy by Local Delivery of Tetracycline*, J. Clin Periodontol 6:83 (1979); and J. Lindhe, et al, *Local Tetracycline Delivery Using Hollow Fiber Devices in Periodontal Therapy*, J. Clin Periodontol 6:141 (1979). However, a problem with this method is that the non-degradable hollow fibers must be removed after treatment.

The present invention solves these and many other problems associated with current methods for the treatment of periodontal disease.

SUMMARY OF THE INVENTION

The present invention relates to the use of time-release biodegradable microspheres for delivery of chemotherapeutic agents to localized sites in the mouth for the treatment of periodontal disease. The method of treatment involves the insertion of biodegradable, time-release microshapes containing chemotherapeutic agents for the treatment of periodontal disease, into the lesion.

In one embodiment of the present invention, biodegradable, time-release microspheres are delivered in a liquid carrying medium by a syringe or other dental carrying instrument. In yet another embodiment of the present invention, a biodegradable matrix or substrate including a chemotherapeutic agent is adhesively attached to the root structure of a tooth. The adhesive utilized to attach the biodegradable matrix or substrate might be biodegradable itself such that after a predetermined time, the adhesive will release or the adhesive might be peeled off by a qualified therapist.

In some embodiments, the walls of the microspheres might have varying thicknesses and/or be made of a different material to provide for release of the chemotherapeutic agent continuously or periodically over an extended interval of time.

In yet other embodiments, the microshapes might have varying configurations depending on the applications.

Additionally, the biodegradable microsphere material might be mixed with chemotherapeutic agent such that as the biodegradable material degrades, the chemotherapeutic agent is gradually released.

It will be appreciated, that the present invention might also be utilized for bone graft material to protect the bone graft material from bacterial invasion and ameliorate bony repair.

The present invention eliminates any requirement for a removal step wherein the medium for transferring the chemotherapeutic agent to the localized area must be removed upon completion of treatment. Furthermore, the present invention provides for better adaptability and patient comfort in general. Additionally, the present invention provides a stronger concentration of chemotherapeutic agent delivered over a longer period of time to a localized area than possible with systemic delivery methods. This reduces the chance of indigenous bacteria developing resistance to the delivered antibiotic.

The embodiment of the present invention utilizing a matrix or substrate provides for substantial release concentration of antibiotic and/or extended duration of release. In addition, the matrix provides delivery of the chemotherapeutic agent to a specific area within the mouth.

These and various other advantages and features of novelty which characterize the invention are pointed out with particularity in the claims annexed hereto and forming a part hereof. However, for a better understanding of the invention, its advantages, and objects attained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views, FIGS. 1A, B, C are cross-sectional views of microspheres containing therapeutic agents in accordance with the principles of the present invention;

FIGS. 2A, B, C are enlarged cross-sectional views of microshapes of various shapes having biodegradable material mixed in with chemotherapeutic agent in accordance with the principles of the present invention;

FIG. 3 is a fragmentary diagrammatic view illustrating positioning of the teeth in the gingiva and bone;

FIG. 4 is a fragmentary diagrammatic view illustrating placement of microspheres containing chemotherapeutic agent in the crevice between the tooth and the gingival tissue;

FIG. 5 is a fragmentary diagrammatic view illustrating placement of microspheres containing chemotherapeutic agent along with bone graft material;

DETAILED DESCRIPTION OF A PREFERRED EMBODIMENT OF THE INVENTION

Figure 6:
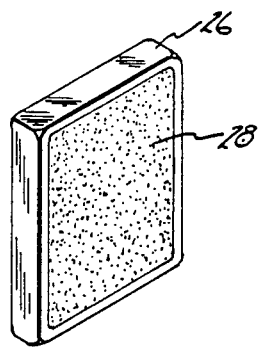
FIG. 6 is an enlarged perspective view of a flexible biodegradable matrix including chemotherapeutic agent thereon.

Referring now to the drawings, shown in FIGS. 1A, B, C are various embodiments of biodegradable microspheres 10 containing chemotherapeutic agent 12. For purposes of illustration, the microspheres 10 shown in FIG. 1 are greatly enlarged. In use, the actual size will approximate one millimeter. As illustrated, the microspheres may have biodegradable outer walls 14 of differing thickness thereby providing for time release of the chemotherapeutic agent over differing intervals of time.

The walls 14 of the biodegradable microspheres 10 might also be made of a different material or substance to provide for interval time release even though the wall thicknesses might be substantially the same. In an alternate embodiment as illustrated in FIGS. 2A, B, C, the microshapes 10 have varying configurations (e.g. circular, rectangular, etc.) and sizes. The chemotherapeutic agent 12 is mixed in with the biodegradable material 15 of the microsphere substrate such that as the biodegradable material degrades, the chemotherapeutic agent is gradually released. It will be further appreciated, that the embodiments shown in FIGS. 2A, B, C might be utilized in conjunction with the embodiments shown in FIGS. 1A, B, C to provide a biodegradable microsphere having a biodegradable wall or shell of a predetermined thickness surrounding biodegradable material mixed in with chemotherapeutic agent.

It will be appreciated that the biodegradable material utilized might be similar to that which is utilized in time release capsules taken orally or other suitable biodegradable materials, safe for use in the body and commonly known.

Illustrated in FIGS. 3 and 4, is the positioning of the biodegradable microspheres 10 in a periodontal pocket or lesion 16 between a tooth 18 and gingival tissue 20, the teeth 18 being securedly positioned in the bone 22. The gingival tissue 20 is displaced from the side of the tooth to facilitate access to the periodontal pocket 16 for placement of the microspheres 10. Utilizing a syringe and a viscous liquid carrying medium or dental carrying instrument, the microspheres 10 are then positioned in the lesion 16. Once in position, the biodegradable microspheres 10 will begin to degrade and release the chemotherapeutic agent 12 to the localized site.

As illustrated in FIG. 5, the biodegradable microspheres 10 might also be intermixed with bone graft material 24 to protect the graft material 24 from bacterial invasion and ameliorate bony repair. As illustrated in FIG. 5, the gingival tissue 20 might be utilized to overlay the microspheres 10 and the bone graft material 24 so as to retain the same in position.

Figure 7A:
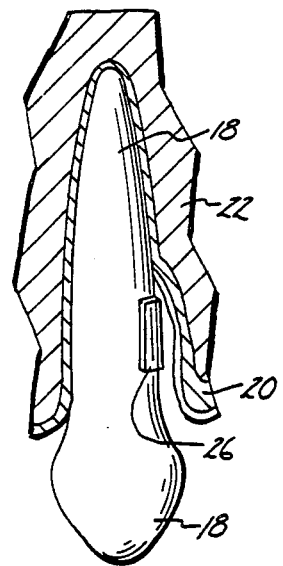
FIGS. 7A, 7B are fragmentary diagrammatic front and side views illustrating placement of the matrix on the root surface of a tooth.
Figure 7B:
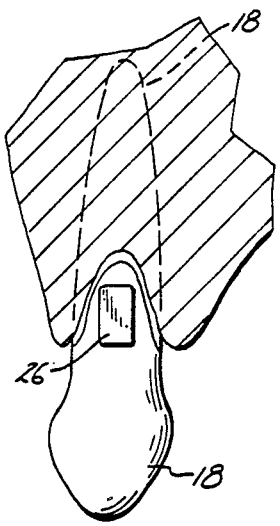

Illustrated in FIGS. 6 and 7A, B is yet another embodiment of the present invention. In this embodiment, a flexible biodegradable matrix or substrate 26 including an adhesive backing 28 is utilized. A chemotherapeutic agent is incorporated into the matrix. The matrix 26 is then positioned on the root surface of the tooth 18 in the periodontal pocket 16. The adhesive backing 28 retains the matrix 26 in position. The adhesive backing might be biodegradable itself such that after a predetermined time interval, the adhesive backing will release or biodegrade after a period of time. In yet other embodiments, the matrix 26 might be removed by a therapist. This embodiment is particularly advantageous in that a substantial mass of chemotherapeutic agent may be utilized thereby increasing the release concentration and/or the duration of the release while providing site specific delivery and retention.

It will be appreciated that the types of antibiotics or other drugs utilized as well as the dosages and duration of treatment will be in accordance with accepted treatment. The present invention addresses the manner in which the chemotherapeutic agents are delivered to the local site.

It is to be understood, however, that even though numerous characteristics and advantages of the invention have been set forth in the foregoing description, together with details of the structure and function of the invention, the disclosure is illustrative only, and changes may be made in detail, especially in matters of shape, size and arrangement of parts within the principle of the invention, to the full extent indicated by the broad general meaning of the terms in which the appended claims are expressed.

What is claimed is:

1. A method for local delivery of chemotherapeutic agents to localized sites in the mouth for treatment of periodontal disease, comprising the steps of:
    (a) displacing gingival tissue away from the surface of the root portion of a tooth so as to form a vacuous cavity between the tooth and the tissue within a peridontal pocket;
    (b) insertion of biodegradable, time-release microshapes encapsulating chemotherapeutic agents, into the vacuous cavity between the tooth and the tissue within the periodontal pocket; and
    (c) allowing the displaced gingival tissue to return substantially to its orginial position for retention of the biodegradable, time-release microspheres in the periodontal pocket whereby the biodegradable, time-release microspheres will begin to degrade and release the chemotherapeutic agents at a localized site.

2. A method in accordance with claim 1, wherein insertion of the biodegradable miscroshapes is accomplished using a syringe apparatus and viscous liquid carrying medium.

3. A method in accordance with claim 1, wherein said biodegradable, time-release microshapes have different time release values thereby assuring generally continuous release of chemotherapeutic agents over an extended period of time.

4. A method in accordance with claim 1, wherein said insertion step includes inserting into the periodontal pocket time release microspheres having different release rates.

5. a method for local delivery of chemotherapeutic agents to localized sites in the mouth for the treatment of periodontal disease, comprising the steps of:
  (a) displacing gingival tissue away from the surface of the root portion of a tooth so as to form a vacuous cavity between the tooth and the tissue within a periodontal pocket
  (b) adhesively positioning a biodegradable matrix including a chemotherpeutic agent thereon, subgingivally on the surface of the root portion of the tooth proximate the vacuous cavity formed between the tooth and the tissue within the periodontal pocket and
  (c) returning the displaced gingival tissue to substantially its original position, the gingival tissue thereby assisting in retention of the chemotherapeutic agent in the periodontal pocket.

6. A method in accordance with claim 5, wherein said matrix is removed after a predetermined period of time.

7. A method in accordance with claim 6, wherein adhesive means utilized for adhesively positioning the biodegradable matrix on the root portion of the tooth is also biodegradable.

* * * * *